United States Patent
Torstensson et al.

(10) Patent No.: US 7,875,136 B2
(45) Date of Patent: Jan. 25, 2011

(54) METHOD FOR MANUFACTURING AN ABSORBENT ARTICLE

(75) Inventors: Robert Torstensson, Göteborg (SE);
Morgan Hansson, Göteborg (SE);
Henrik Carlén, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 325 days.

(21) Appl. No.: 12/085,948

(22) PCT Filed: Dec. 7, 2005

(86) PCT No.: PCT/SE2005/001854

§ 371 (c)(1),
(2), (4) Date: Jun. 3, 2008

(87) PCT Pub. No.: WO2007/067103

PCT Pub. Date: Jun. 14, 2007

(65) Prior Publication Data

US 2009/0194218 A1  Aug. 6, 2009

(51) Int. Cl.
*B32B 41/00* (2006.01)
(52) U.S. Cl. .................. 156/64; 156/361; 156/378; 156/379
(58) Field of Classification Search ............... 156/64, 156/361, 378, 379; 101/481, 485, 486
See application file for complete search history.

(56) References Cited

U.S. PATENT DOCUMENTS

| | | | |
|---|---|---|---|
| 3,616,898 A * | 11/1971 | Massie | .................. 206/216 |
| 4,826,550 A | 5/1989 | Shimizu et al. | |
| 5,045,135 A | 9/1991 | Meissner et al. | |
| 5,197,958 A | 3/1993 | Howell | |
| 5,989,370 A * | 11/1999 | Wannebo | .................. 156/73.1 |
| 6,093,474 A | 7/2000 | Sironi | |
| 6,224,699 B1 * | 5/2001 | Bett et al. | .................. 156/64 |
| 6,574,520 B1 | 6/2003 | Liu et al. | |

FOREIGN PATENT DOCUMENTS

| | | |
|---|---|---|
| EP | 1 035 818 A | 9/2000 |
| EP | 1 199 057 A1 | 4/2002 |
| JP | 3161511 | 7/1991 |
| JP | 4241115 | 8/1992 |
| JP | 8027653 | 1/1996 |
| JP | 2001-055623 | 2/2001 |
| JP | 2001-123088 | 5/2001 |
| JP | 2002-138322 | 5/2002 |

OTHER PUBLICATIONS

PCT/ISA/210.
PCT/ISA/237.

* cited by examiner

*Primary Examiner*—George R Koch, III
(74) *Attorney, Agent, or Firm*—Buchanan Ingersoll & Rooney PC

(57) ABSTRACT

A method for manufacturing an absorbent hygiene article having a plurality of components that are joined together during the manufacturing process. Thermochromic fibres are incorporated in a component web, component or a selected area thereof, said thermochromic fibres being adapted to change colour between a contrasting colour to a less contrasting colour. A colour change of said thermochromic fibres is induced during one step of the manufacturing process and the presence of the thermochromic fibres being in their contrasting state is detected by a detection means. A measure in the process control is actuated in response to the detected presence of thermochromic fibres in their contrasting state.

21 Claims, 4 Drawing Sheets

METHOD FOR MANUFACTURING AN ABSORBENT ARTICLE

This application is a national stage entry of PCT/SE2005/001854, filed Dec. 07, 2005.

TECHNICAL FIELD

The present disclosure refers to a method for manufacturing an absorbent hygiene article such as a diaper, a pant diaper, a sanitary napkin, an incontinence guard comprising a plurality of components that are joined together during the manufacturing process. The disclosure provides a method for improved control of certain manufacturing steps.

BACKGROUND

Absorbent articles comprise a plurality of components, like web materials constituting the outer and inner coversheets of the article, absorbent layers etc., which are joined together for example by thermobonding, ultrasonic welding or gluing in a manufacturing process in high speed. Other components like elastic threads, fastening tabs, waist bands, side panels, belts etc. may also be incorporated in articles like diapers, pant diapers and incontinence guards. All these components must be applied and fastened in a correct position of the article. Cutting operations, in which selected lengths of materials are cut off, are also occurring in the manufacture of absorbent articles, and the cut off has to be made in a precise location. Control and synchronization of the joining of the different components in an absorbent article, application of a substrate to a selected area of a component, control of thermobonding, welding and glue patterns as well as of cutting operations, is of critical importance for the product quality.

U.S. Pat. No. 5,045,135 discloses a method for controlling the cut off register in a diaper machine. A diaper web having a plurality of longitudinally spaced apart absorbent pads thereon passes a detection means detecting the edge of the pad. The cut off means is controlled by the signals from the detection means.

EP-A-1 199 057 discloses a method for manufacturing an absorbent article having a predetermined pattern arranged at a predetermined position of the article. The pattern is printed on a continuously moving web material fed at a selected speed and is cut into selected lengths at a predetermined position. The position of the printed pattern is detected and the signal is used for controlling the feeding speed of the web, thereby obtaining the printed pattern at a correct location with respect to the cut off position.

In these two documents an edge of a pad and a printed pattern respectively is visually detected and used for controlling certain process steps. However such product features which are visually detectable at a certain position that may be used for process control are not always available and it therefore exists a need for improvement of the flexibility of the process control.

OBJECT AND SUMMARY

An object of the present disclosure is to provide a solution to the above problem and to provide a more flexible system for controlling and synchronizing certain process steps in the manufacturing of absorbent articles.

These and further objects have been solved by incorporating thermochromic fibres in a component web, component or selected area thereof, said thermochromic fibres being adapted to change colour between a contrasting colour to a less contrasting colour; inducing a colour change of said thermochromic fibres during one step of the manufacturing process; detecting the location of the thermochromic fibres being in their contrasting detectable colour state by a detection means; actuating a measure in response to the location of the thermochromic fibres.

The disclosure makes it possible to avoid disturbing synchronization marks on the article and avoids the need for cutting off material having synchronization marks thereon.

In one embodiment the colour change of the thermochromic fibres is induced prior to the detection step, wherein the thermochromic fibres will change to a contrasting colour that is detectable by said detection means. Preferably the colour change is reversible and will disappear after detection by said detection means.

In an alternative embodiment the thermochromic fibres incorporated in said article have a contrasting colour that is detectable by said detection means, wherein the colour change of the thermochromic fibres is induced after the detection step. Preferably the colour change is irreversible and such that the thermochromic fibres will become less contrasting to the surrounding areas of the article.

In one aspect of the disclosure, data is submitted from said detection means to control means for control of a process step and/or a process parameter; said process step and/or process parameter being controlled in response to the data submitted from the detection means.

In a further aspect the position and/or configuration of a colour detected area provided by said thermochromic fibres is by said control means compared with a set value and/or detected location of a component of said article, said control means inducing adjustment of one or more process steps and/or process parameters when the position and/or configuration of said colour detected area deviates from said set value and/or said detected location. Examples of such process steps and/or process parameters are: temperature, position of a component of the article and/or process equipment, process speed, stretching of a web material.

According to one aspect of the disclosure, said colour detected area is a thermobonding pattern, a weld pattern a glue pattern or the like, in which the bonding process has induced a colour change in the bonded areas.

In one embodiment the position of a colour detected area provided by said thermochromic fibres is used as a synchronizing mark for joining two or more components of the article together in selected areas.

In a further embodiment the position and/or configuration of a colour detected area provided by said thermochromic fibres is by said control means compared with a set value and/or detected location of a component of said article and that an alarm signal is generated when the position and/or configuration of said colour detected area deviates from said set value and/or said detected location.

In a still further aspect of the disclosure, the thermochromic fibres change colour at a temperature of between 45 and 150° C., preferably between 50 and 130° C., more preferably between 50 and 120° C. and most preferably between 60 and 120° C.

BRIEF DESCRIPTION OF DRAWINGS

The disclosure will be described in the following in greater detail by way of examples and with reference to the accompanying drawings, in which.

DEFINITIONS

Absorbent Article

Figure 1:
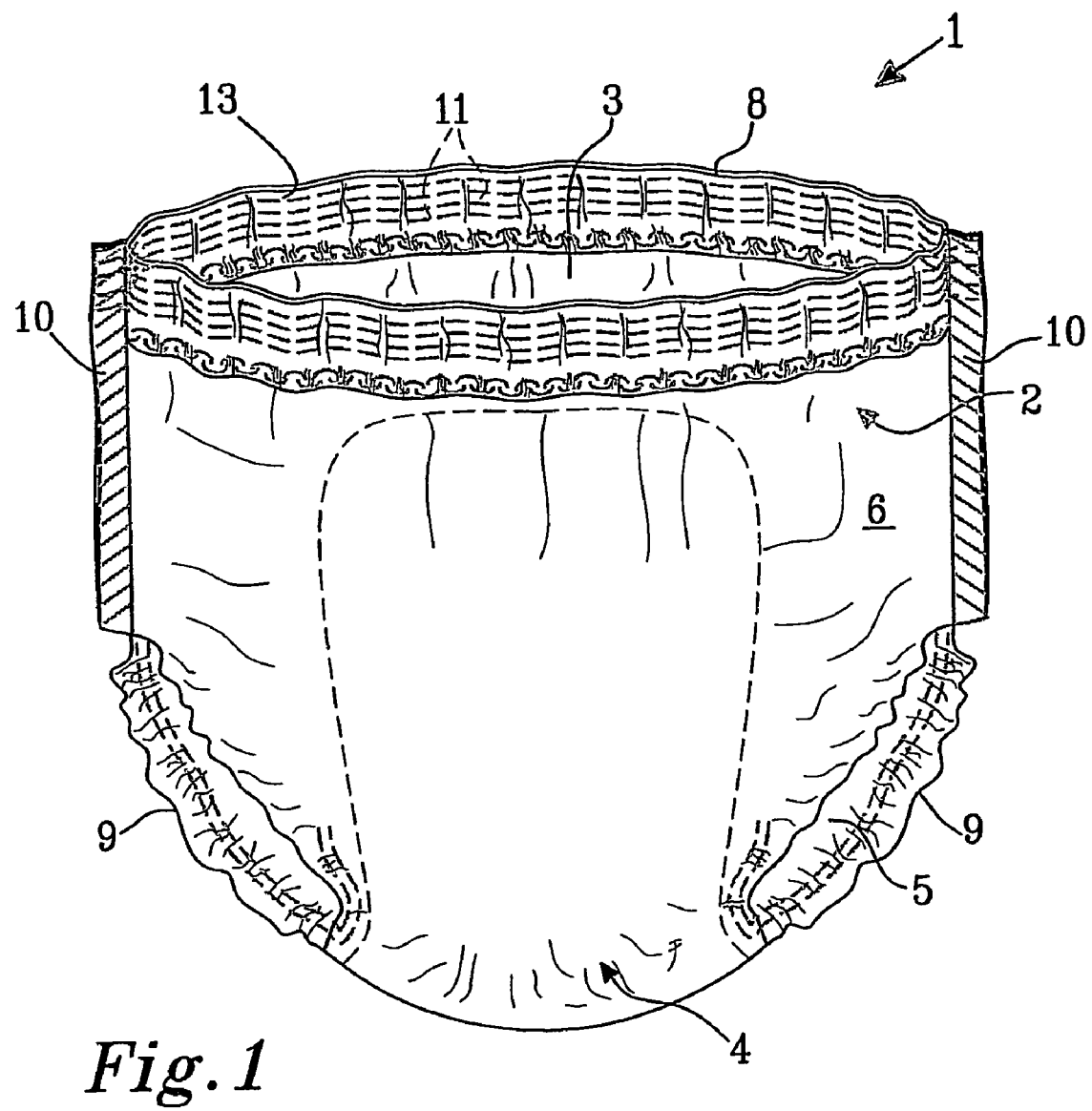
FIG. 1 is a perspective view of an absorbent article in the form of a pant diaper.

The term "absorbent article" refers to products that are placed against the skin of the wearer to absorb and contain body exudates, like urine, faeces and menstrual fluid. The disclosure mainly refers to disposable absorbent articles, which are articles that are not intended to be laundered or otherwise restored or reused as an absorbent article after use. The absorbent article comprises a plurality of components that are joined together in the manufacturing process, such as an inner liquid permeable cover, an outer liquid impermeable cover, an absorbent structure, an acquisition layer, elastic members, fastening means etc.

Inner Liquid Permeable Cover

The inner liquid permeable cover forms the inner cover of the absorbent article and in use is placed in direct contact with the skin of the wearer. The inner liquid permeable cover can comprise a nonwoven material, e.g. spunbond, meltblown, carded, hydroentangled, wetlaid etc. Suitable nonwoven materials can be composed of natural fibres, such as woodpulp or cotton fibres, manmade fibres, such as polyester, polyethylene, polypropylene, viscose etc. or from a mixture of natural and manmade fibres. The inner liquid permeable cover material may further be composed of tow fibres, which may be bonded to each other in a bonding pattern, as e.g. disclosed in EP-A-1 035 818. Further examples of inner liquid permeable cover materials are porous foams, apertured plastic films, laminates of film/nonwovens etc. The materials suited as inner liquid permeable cover materials should be soft and non-irritating to the skin and be readily penetrated by body fluid, e.g. urine or menstrual fluid. The inner liquid permeable cover may further be different in different parts of the absorbent article.

Outer Liquid Impermeable Cover

The outer liquid impermeable cover forms the outer cover of the absorbent article at least on the core area thereof. The outer liquid impermeable cover can comprise a thin plastic film, e.g. a polyethylene or polypropylene film, a nonwoven material coated with a liquid impervious material, a hydrophobic nonwoven material, which resists liquid penetration, or a laminate, e.g. of a plastic film and a nonwoven material. The outer liquid impermeable cover material may be breathable so as to allow vapour to escape from the absorbent structure, while still preventing liquids from passing through. Examples of breathable outer liquid impermeable cover materials are porous polymeric films, nonwoven laminates from spunbond and meltblown layers, laminates from porous polymeric films and nonwoven materials.

Absorbent Structure

The "absorbent structure" is the absorbent structure disposed between the two covers of the absorbent article. The absorbent structure can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent structure.

It is conventional in absorbent articles to have absorbent structures comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent structure may be varied to be suited for different uses such as for infants or for adult incontinent persons.

Acquisition Layer

A so called acquisition layer may be arranged between the inner liquid permeable cover and the absorbent structure. The acquisition layer is adapted to quickly receive and temporarily store discharged liquid before it is absorbed by the underlying absorbent structure. Such acquisition distribution layers are well known in the art and may be composed of porous fibrous waddings or foam materials.

Fastening Means

Fastening means are used to releasably attach different components of an absorbent article together during use, for example attaching the front an back portions of a diaper together to form a pant-like shape. Fastening means are usually in the form of mechanical fasteners, such as hook and loop fasteners (Velcro®), or adhesive tapes.

Elastic Members

Elongated elastic members are used on some articles to improve the fit of the article in certain areas, such as the leg openings and/or the waist area. The elastic members, such as elastic threads, are bonded to a material layer or between material layers. The elastic members may alternatively be of a material that is activatable by some means, for example by heat, to an elastified state, wherein they may be attached to the article in an unstretched inactivated state and are subsequently activated to a contracted elastic state.

Themochromic Fibres

Thermochromic pigments are organic compounds that effectuate a reversible or irreversible colour change when a specific temperature threshold is crossed. A thermochromic pigment basically comprises three main components: (i) an electron donating colouring organic compound, (ii) an electron accepting compound and (iii) a solvent reaction medium determining the temperature of the colouring reaction to occur.

A thermochromic particulate material which may be used according to the disclosure may be prepared from particles of a non-thermoplastic resin having enclosed therein the three components of electron-donating chromogenic substance, electron-accepting substance and solvent by coating the particles with a hydrophilic high-molecular-weight compound. The thermochromic particulate material, when incorporated into a vinyl chloride plastisol, remains free of the influence of the plasticizer, stabilizer, lubricant or the like contained in the plastisol and retains very high stability even when heated.

The process for preparing a molded product of thermochromic polyvinyl chloride is characterized by incorporating a thermochromic particulate material into a vinyl chloride plastisol comprising a vinyl chloride resin, plasticizer, stabilizer, lubricant and filler. Thereafter molding the resulting mixture. The thermochromic particulate material being prepared from particles of a non-thermoplastic resin having encapsulated therein the three components of electron-donating chromogenic substance, electron-accepting substance and solvent by coating the particles with a hydrophilic high-molecular-weight compound.

A molded thermochromic polyvinyl chloride material can thereby be prepared which reliably undergoes a reversible color change with a change of temperature. A material like this becomes skin-colored when the temperature rises beyond about 40° C. The color change is reversible. This is further described in U.S. Pat. No. 4,826,550.

Such thermochromic pigments and the mechanism bringing about the temperature triggered colour change to occur are well-known in the art and are for example described in U.S. Pat. No. 4,826,550 and U.S. Pat. No. 5,197,958.

Thermochromic or temperature sensitive colour changing fibres are known from the textile field to be used in clothing, sport equipment etc. The fibres are either produced by blending a thermochromic pigment in the base resin from which the fibres are to be produced, for example a polyolefin, such as polyethylene or polypropylene, polyester, polyvinyl alcohol etc. or by using a thermochromic colouring liquid for the fibres. The production of temperature sensitive colour-changing fibres are disclosed in for example JP2002138322 and JP2001123088. The fibres change colour at a selected temperature. The change of colour is either reversible or irreversible.

An example of a fibre which can be used according to the disclosure is a thermochromic fibre which is partly characterized in that the flexural modulus of elasticity of a base resin is within the range of 300-1,500 MPa in the temperature-sensing color-changing fibre. The fibre is formed by melt blending a thermally color-changing pigment in a dispersed state in the base resin of a polyolefin resin and/or the polyolefin resin blended with a thermoplastic resin. This fibre is earlier used in the textile field. The inventors have found that fibres with this characteristics may also be suited for use in absorbent articles, especially diapers. The fibre is further described in JP 2002-138322.

In another embodiment of the disclosure, the thermochromic fibre is a thermosensitive color-changing acrylic synthetic fibre. Such fibres may be constituted of a plurality of long fibres or short fibres of a thermosensitive color-changing synthetic acrylic fibre having 1-100 μm outer diameter of monofilament. The fibres may be formed by dispersing 0.5-40 wt. % of a thermosensitive pigment containing essential three ingredients of (A) an electron donating coloring organic compound, (B) an electron-accepting compound and (C) a reaction solvent determining the occurrence temperature of a coloring reaction of the ingredients A and B. This is described in more detail in JP 2001-055623.

Another thermochromic fibre according to the disclosure is a conjugate fibre which is excellent in reversible color changeability, brightness and durability. It may be produced by using a (1) thermal color changing polyester composed of a thermal color changing material-containing thermoplastic polyester and (2) a fibre-forming polyester in which $\geq 50$ mol % of an acid component is terephthalic acid; 0-50 mol % thereof is isophthalic acid and $\geq 70$ mol % of a diol component is composed of butanediol and/or hexanediol are subjected to melt conjugate spinning. The resultant yarn is then drawn to afford the objective fibre which is conjugate fibre, containing a part composed of the component (1) joined to a part composed of the component (2) and having $\geq 1.5$ g/denier fibre strength, $\leq 80$% fibre elongation and $\leq 25$% shrinkage factor in boiling water. This is further described in JP 4241115.

Another fibre which is excellent in friction durability and mechanical characteristics which may be suitable for the embodiments of the disclosure can be achieved by using a low-melting thermoplastic resin containing a temperature-sensitive color changing granular substance as a core component and a high-melting thermoplastic resin as a sheath component at a specific ratio.

The fibre is obtained by mixing an acid developing substance (e.g. 3,3'-dimethoxyfluoran) with an acidic substance (e.g. phenol) and a solvent (e.g. octyl alcohol), granulating the resultant mixture and carrying out conjugate spinning of a thermoplastic resin (e.g. polypropylene), having $\leq 230°$ C. melting point and containing 1-40 wt. % resultant temperature-sensitive color changing granular substance. The granules having 1-50 μm grain diameter and $\geq 220°$ C. heat resistance as a core component and a thermoplastic resin (e.g. nylon) having $\leq 280°$ C. melting point as a sheath composition at (1/9)-(9/1) weight ratio of core component:sheath component, having a smooth surface and excellent in mechanical characteristics with a high level of temperature-sensitive color changing function. This method is further described in JP 3161511.

The temperature sensitive pigment used in the thermochromic fibres has preferably an average particle size of 0.5-50 μm, preferably 0.5-30.0, even more preferably μm 0.5-15.0 μm measured by appropriate ASTDM standard method.

The thermosensitive pigment may preferably be of a microcapsule type which is known in the art of thermosensitive pigments.

DESCRIPTION OF PREFERRED EMBODIMENTS

The pant diaper 1 disclosed in the drawings typically comprises a front region 2, a back region 3 and a crotch region 4 between the front region and back region. In its most common form the pant diaper comprises a liquid pervious inner cover 5, a liquid impervious outer cover 6 and an absorbent core 7 disposed between the inner and outer covers. The pant diaper is intended to enclose the lower part of the wearer's trunk like a pair of absorbent pants. The front and back regions 2 and 3 may have different material composition than the crotch region, for example only the crotch region may contain liquid impermeable material.

The front and back regions 2 and 3 are joined to each other along two opposite side edges 2a and 3a and 2b and 3b respectively, to define a waist-opening 8 and a pair of leg-openings 9. The front and back regions 2 and 3 are joined along said side edges 2a and 3a and 2b and 3b respectively, for example by adhesive, ultrasonic welding, heat sealing or the like, so as to form side seams 10. The front and back regions 2 and 3 can either be joined along their side edges with the inner cover 5 facing inwards in the side seams, as is shown in the drawings. Alternatively they are joined in an overlapped manner with the inner cover 5 of either the front or back region facing the outer cover 6 of the opposite region.

The waist area and at least a part of the leg opening area are elasticized. The elastification is usually accomplished by a plurality of elastic members, such as elastic threads 11 and 12, contractably affixed to a material layer or between material layers. The elastification of the waist area is according to the embodiment shown in the drawings accomplished by an elastic waist band 13 comprising a substantially non-elastic non-woven material 14 that is elasticized by elongate elastic members 11, such as elastic threads, contractably affixed inside the waist band 13.

The article has a longitudinal direction y and a transverse direction x.

The inner cover 5 and the outer cover 6 extend outward beyond the peripheral edges of the absorbent structure 7 and have their inner surfaces bonded to each other, e g by gluing or welding by heat or ultrasonic. The inner and outer cover materials may further be bonded, e.g. by adhesive, to the absorbent structure.

The absorbent articles in the form of a pant diaper shown in the drawings is only one example of a personal care absorbent article and the embodiments of the disclosure may be applied to any type of absorbent article falling under the definition given above, including so called open diapers in which the front and back portions are fastened together by fasteners, such as adhesive tape or hook-and-loop type fasteners, belted diapers wherein belt members are used to attach the article around the waist of the wearer, incontinence pads, sanitary napkins and panty liners intended to be worn in the panties of the wearer etc.

The absorbent article according to the present disclosure contains thermochromic fibres. As mentioned above thermochromic fibres are fibres having incorporated therein a thermochromic pigment. The thermochromic pigment basically comprises three main components. (i) an electron donating colouring organic compound, (ii) an electron accepting compound and (iii) a solvent reaction medium determining the temperature of the colouring reaction to occur.

Such thermochromic pigments and the mechanism bringing about the temperature triggered colour change to occur are well-known in the art and are for example described in U.S. Pat. No. 4,826,550 and U.S. Pat. No. 5,197,958. The first mentioned document discloses molded products of polyvinyl chloride, having incorporated therein thermochromic particulate material. The last mentioned document discloses a wetness indicating diaper having a thermochromic ink printed on the diaper backhseet.

A description of fibres having incorporated therein such thermochromic pigments can be found in any of the following Japanese published patent applications: JP 2002-138322 disclosing thermally colour-changing fibres for various textile applications, such a imitated wool; JP 2001-123088 disclosing a reversibly thermochromic colouring liquid for fibres and fabrics made therefrom; JP 2001-055623 disclosing thermosensitive colour-changing synthetic acrylic fibres; and JP 8027653 disclosing a thermally colour-changing nonwoven material containing a certain amount of reversibly colour-changing crimped fibres.

The thermochromic pigment may be incorporated in the base resin of the fibres in the form of microcapsules or as a colouring liquid for the fibres.

The entire fibre may be coloured by the thermochromic pigment, or the fibre may be of a bicomponent type, wherein either the core or the outer casing of the fibre is provided with the thermochromic pigment. The change of colour may either be reversible or irreversible.

Figure 2:
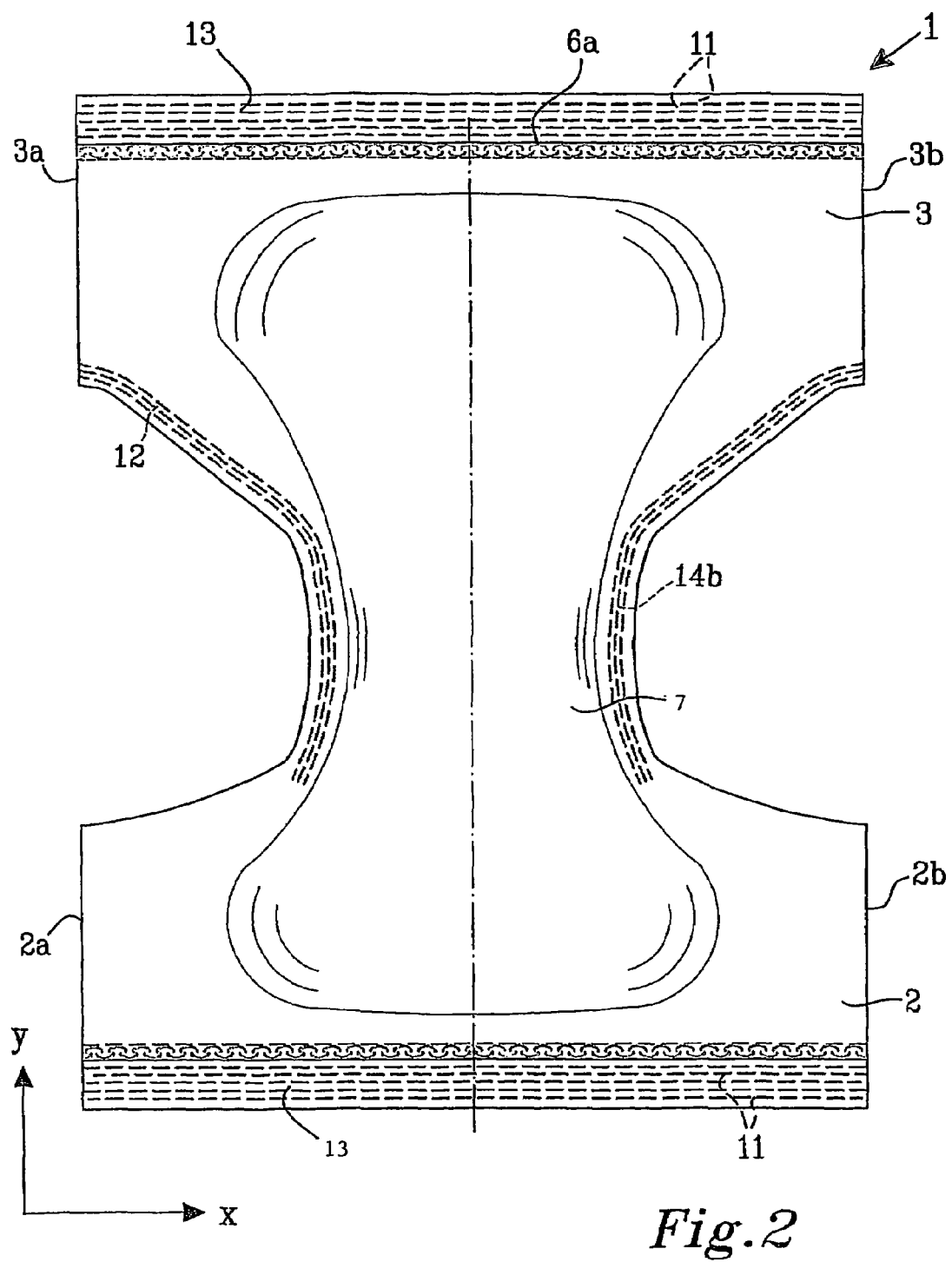
FIG. 2 is a plan view of the pant diaper in its flat, uncontracted state prior to formation as seen from the body facing side.

According to the disclosure the thermochromic fibres are used in the manufacturing process as an indicator and/or synchronization marking in one or more process step. One purpose may be to control one or more process steps and/or process parameters. Another purpose may be to generate an error or alarm signal when a detected value deviates from a set value, indicating that there is something in the manufacturing process that needs to be corrected. Below an example will be described of parts of a manufacturing process for manufacturing a pant diaper according to the embodiment shown in FIGS. 1 and 2. It will be indicated how thermochromic fibres may be used for controlling certain process steps.

The thermochromic fibres may, depending on the intended purpose, be incorporated in any suitable component of the absorbent article, such as the outer cover, the absorbent structure, a layer of an absorbent structure, the inner liquid pervious cover, fastening tabs, elastic members etc. The thermochromic fibres may alternatively be applied, for example sprayed, onto a component of the absorbent article during the manufacturing process.

The colour-changing properties of the thermochromic fibres may be such that they when exceeding a certain temperature (the trigger temperature) change from a "colourless" or "faint" colour to a colour that is contrasting to the surrounding material. The colour change may in this case be induced by a process step, for example heat calendaring, thermobonding, welding, application of hot glue etc. Preferably the colour change is reversible, so that after a certain period of time the fibres revert to their less contrasting colour and will not be visible or at least not so pronounced visible on the finished product.

Alternatively the colour-changing properties of the thermochromic fibres is such that they when introduced in a component of the absorbent article have a contrasting colour. When exerted to a temperature above the trigger temperature they will change to a less contrasting colour or even be colourless. This trigger temperature may also be induced by a process step as indicated above. However in this case detection of the thermochromic fibres must take place before the detection step. The trigger temperature may be the same as indicated above. The colour-change should in this case be irreversible.

Figure 3:
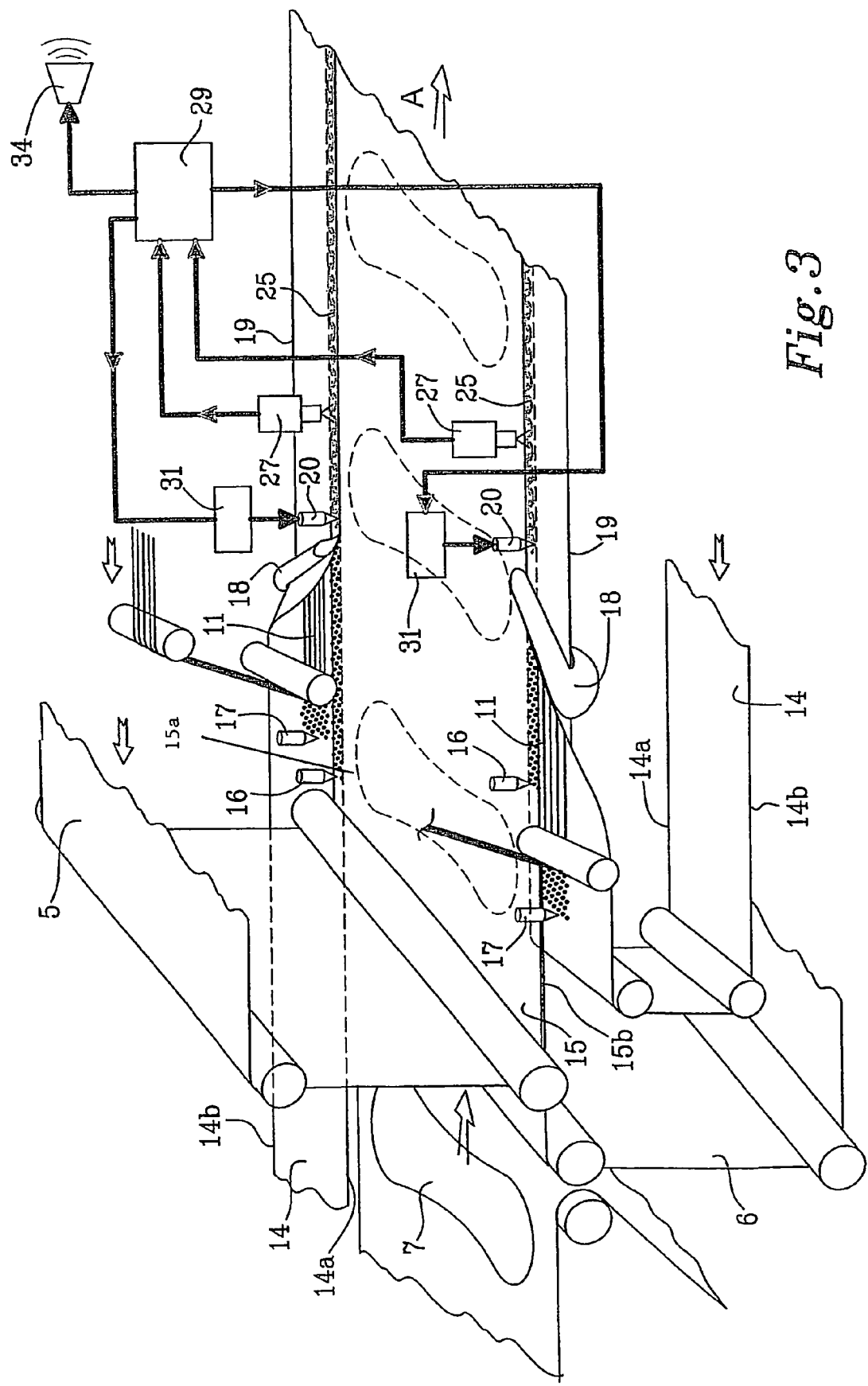
FIG. 3 is a schematic perspective view of a length of a production line for manufacturing the pant diaper.
Figure 4:
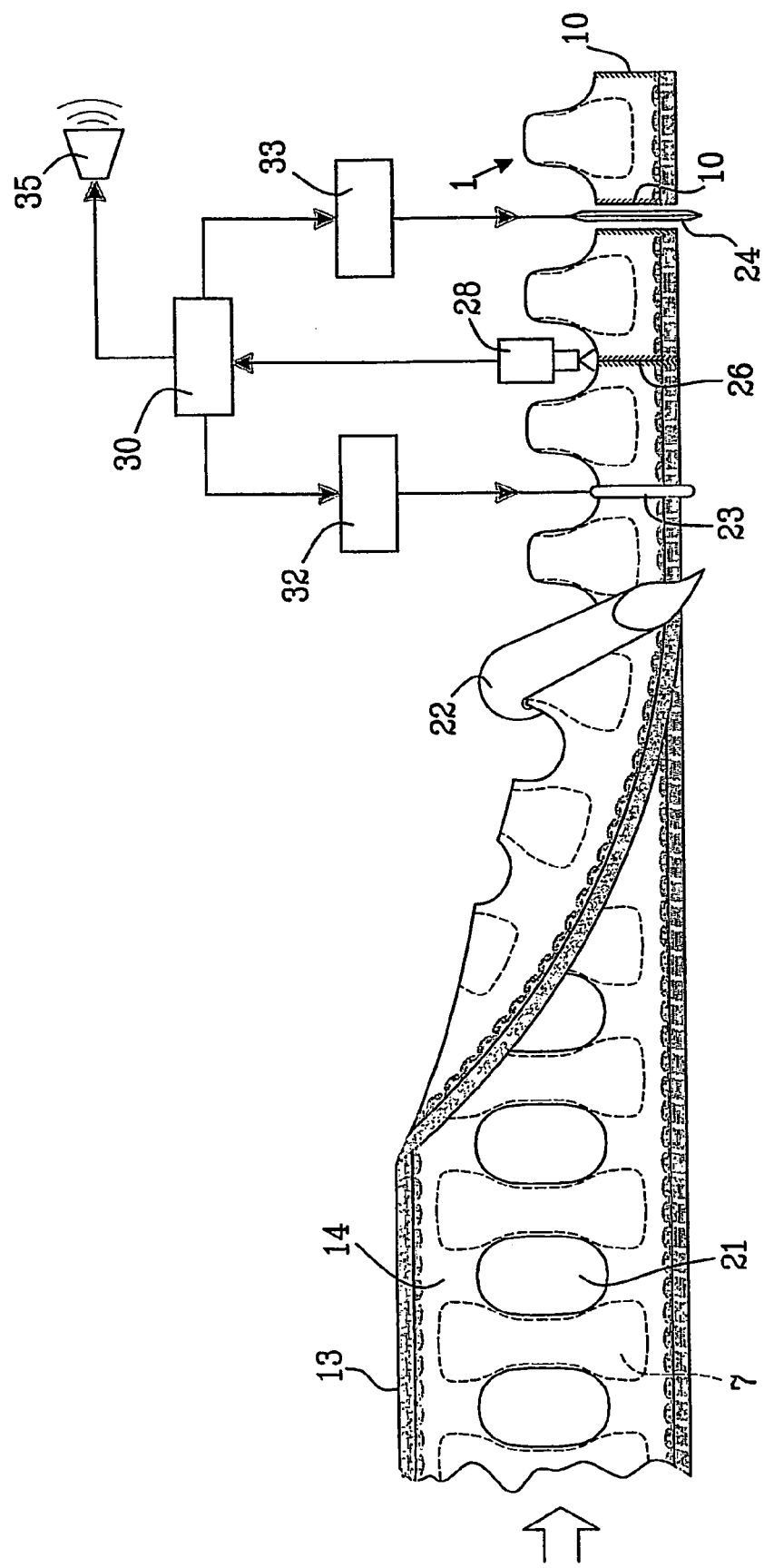
FIG. 4 is a schematic view of a later part of the production line.

The pant diaper may be manufactured by a process parts of which are illustrated in FIGS. 3 and 4. The various components of the absorbent article are united on a (not shown) conveyor belt running in a direction of travel denoted by arrow A. A pair of continuous lengths of substantially non-elastic web material 14 intended to form the waistband 13, are fed in parallel and spaced apart a selected distance along the conveyor belt. The waistband web materials 14 have two longitudinal side edges 14a and b and are along their longitudinal edges 14a facing each other brought together with a continuous length of body panel material 15 intended to form the front, back and crotch regions 2, 3 and 4 of the article. The body panel material 15 comprises inner and outer covers 5 and 6, having absorbent structures 7 enclosed there between at spaced locations.

The body panel material 15 has two longitudinal side edges 15a and b and is brought together with the waistband web material 14 and joined by gluing, ultrasonic welding 16 or the like in an overlapping manner, so that the their respective longitudinal side edges overlap at least about 5 mm.

A plurality of elongate elastic members 11 are then supplied and joined to each of the waistband web materials 14 in any suitable manner known in the art, for example by gluing 17. The elongate elastic members 11 are supplied in a selectively tensioned manner or they may alternatively be supplied in a substantially untensioned manner and subsequently be activated to tensioned state, for example by heat. In the latter case the elongate elastic members 11 are of a specific type of elastomeric material, referred to as a heat-elasticizable material.

After supplying the elongate elastic members 11 to the waistband web materials 14, said web materials pass through a folding board 18 each, which continuously folds the respective waistband web material 14 transversely to the feeding direction A along a fold line 19 and over the elongate elastic members 11. The free longitudinal edge 14b of each waistband web material 14 is subsequently secured to the respective body panel material 15 to its longitudinal edge 15a in an overlapping manner on the opposite side thereof as the other longitudinal edge 14a of waistband web material, which has already been secured to the body panel web material 15. Alternatively both side edges 14*a* and *b* of the waistband web material 14 are joined to the same side of the body panel web material 15. The joining of the overlapping edges of web materials 14 and 15 made ultrasonic welding or the like by a device denoted with the numeral 20.

The joining effect, for example the ultrasonic weld, provided by the second joining device 20 may be considerably stronger than the joining effect provided by the first joining device 16, which may only provide for example a slight tack weld sufficient to keep the overlapping edges of the two material webs 14 and 15 together to the next joining station 19. The folded waist band web material 14, with the elongate elastic members 11 enclosed therein, will form the elastic waistband 13 of the absorbent article.

Alternatively to folding the waist band web material 14, a further waist band web material may be supplied and joined in an overlapping manner to the longitudinal edge 14*a* of the body panel web material 15. The free side edges of the two non-elastic web materials are joined to each other either in a preceding or subsequent step. In this case each of the waist band web materials 14 are of a width corresponding to the width of the waistband 13.

It is understood that the different process steps of joining the different material webs may take place in any order. Likewise, the disclosure is applicable on production having the articles oriented in cross direction, as shown in FIG. 3, as well as production with the articles oriented in length direction on the production line.

Further components like elongate elastic members forming leg elastics 12 are attached to the production web in a suitable manner known in the art. Leg openings 21 are cut in the production web and the pant diaper is formed by folding by means of folding board 22 the production web in double in the production direction, joining the folded production web, for example by ultrasonic welding by a device denoted 23, intermittently transverse to the feeding direction from the waist opening to the leg openings to form side seams 10 and subsequently cutting by means of a cutting device 24 along the side seams to form separate pant articles 1. This is illustrated in FIG. 4.

Having thermochromic fibres incorporated in or between the inner 5 and/or outer covers 6 and/or waist band material 13, will result in a colour change of said fibres triggered by the ultrasonic welding. This will result in a welding pattern 25 and 26 that is contrasting from the surrounding parts of the material web and thus easily detectable. In the embodiment illustrated in FIGS. 3 and 4 weld patterns 25 and 26 are made in the waist band area and in the side seams 10. These weld patterns are detected by image recording means 27 and 28, for example in the form of a so called Vision-system, which is a system for automatic inspection, for example delivered by Novotek Sverige AB. An image of the welding pattern in the weld seams is created, which develops a video signal that is delivered to an image digitizer and analyzer unit 29 and 30 respectively comparing the recorded image against a previously established value range. If the recorded image deviates from the established value range (set value) a signal is sent to a correction and control unit 31, 32 and/or 33 respectively, which may have one or more of the following functions:

a) Controlling the ultrasonic welding devices for example with respect to energy input, positioning of the device etc.

b) Controlling positioning, web speed and/or web tension of the web materials introduced in the ultrasonic welding device;

c) Controlling and synchronizing the cutting device 24 in response to the location of the welding pattern;

d) Triggering an alarm signal 34, 35 to indicate that measures need to be taken in the process control.

In the last mentioned case the measures could be to check whether an equipment, for example an ultrasonic horn or pattern roll is worn out and needs to be replaced, or to check whether one or more process steps or parameters, such as temperature, web speed, web tension, positioning of equipment or web materials need to be adjusted.

The position of the weld seam may also be checked with respect to a fixed point in the web material, for example en edge contour of the absorbent structure 7, which is also detectable by the image recording means 28.

The example shown and described with respect to FIGS. 3 and 4 is only illustrating one embodiment of the disclosure. It is understood that the principle of the present disclosure of utilizing thermochromic fibres in the process control in a manufacturing process for absorbent articles may be modified in many different ways. Some further examples are listed below:

Synchronization marking for example for attaching a component, for example a fastening tab, at a specified location on another component;

Detection of a glue pattern created by the application of hot glue to a web material;

Detection of a thermobonding pattern created by a heated roll causing fusing of at least a part of the components of a web material;

Detection of a cut in a web material.

Detection of de-elasticized parts of an elastic component, such as an elastic nonwoven, a laminate of nonwoven and film or a nonwoven laminate, wherein the de-elastification in selected areas has been accomplished by heat treatment, ultrasonic bonding or the like In some of the above examples a process step preceding the detection device may cause a temperature increase triggering a colour change of the thermochromic fibres. In other of the examples thermochromic fibres may be used that have a contrasting colour initially.

In some cases the configuration of a certain entire area, such as a welding pattern, containing thermochromic fibres having a contrasting colour, is detected by an image recording device, as described above. In other cases only the presence of an area containing thermochromic fibres or a contrast line between an area containing contrasting thermochromic fibres and an adjacent area is detected. In such cases a simpler sensor may be used instead of an image recording device.

In case thermochromic fibres are used that must change colour before detection, the response time of the thermochromic fibres, i.e. the time it takes for the colour change to occur from having been exerted to the trigger temperature, should be short enough to enable a detection by the image recording means or sensor, or in other words the distance between the process equipment triggering the colour change, e g welding, thermobonding or gluing device, and the image recording means or sensor should be large enough for making a detection possible. It is desired that the response time is less than 3 seconds, preferably less than 2 seconds and more preferably less than 1 second from when the fibres have been exerted to the trigger temperature. A high impact temperature (high above the trigger temperature) on the thermochromic fibres will give a faster colour change than a low impact temperature (close to the trigger temperature).

The colour change to a contrasting colour is preferably reversible, so that after a certain period of time, the fibres revert to their initial colourless or at least less contrasting colour, so that they will be more or less invisible in the final product. The reverting time should be long enough to make the detection possible, or in other words the distance between the process equipment triggering the colour change, e g welding device, and the image recording means or sensor should be short enough for the colour change to remain past the detection device.

For applications where it is desired to maintain the colour change of the thermochromic fibres in the final product, e g for permanent visualization of a bonding pattern, irreversible thermochromic fibres may be used.

As mentioned above thermochromic fibres may alternatively be used that initially have a contrasting colour. After their use as for example synchronization marking or product control a colour change is induced by a heating step, so that they change to a colourless or at least less contrasting colour.

The thermochromic fibres may be incorporated substantially homogeneously in an entire layer and mixed with other fibres in the layer. Alternatively they are incorporated only in selected parts of a layer. A further alternative is that a separate fibrous layer, for example a nonwoven layer, produced mainly (at least 50%) or even entirely from thermochromic fibres as the sole fibrous component is incorporated in the article. An appropriate amount of the thermochromic fibres in for example an inner coversheet, an acquisition layer, an absorbent structure or a layer in an absorbent structure or an outer coversheet, is at least 1% by weight, preferably at least 5%, more preferably at least 10% by weight and most preferably from 20 to 70% by weight based on the weight of said fibrous layer in areas in which said thermochromic fibres are distributed. Thus if the thermochromic fibres are distributed in only half of the layer, the weight-% should be based on the weight of that half part of the layer.

The rest of the fibres, with which the thermochromic fibres are mixed, may vary depending on which component of the absorbent article the thermochromic fibres are incorporated in, if it for example is a backsheet material, a coversheet, a backsheet or an absorbent structure. Thus the rest of the fibres may be cellulosic fibres, polyethylene, polyproplyene, polyester, polylactide, viscose fibres and the like.

In one embodiment the rest of the fibres with which the thermochromic fibres are mixed are made of the same polymeric material as the thermochromic fibres. Thus if the thermochromic fibres comprises polypropylene having a thermochromic pigment incorporated therein, these thermochromic fibres may be mixed with other polypropylene fibres with no thermochromic pigment in them.

In case a fibrous layer consisting of thermochromic fibres as the sole fibrous component is used, such layer should have a basis weight of at least 7, preferably at least 10 and more preferably at least 15 g/m$^2$.

As mentioned above the thermochromic fibres may alternatively be applied, for example sprayed, onto a component of the absorbent article during the manufacturing process.

Two or more types of thermochromic fibres may be used in the same article. These different thermochromic fibres may have different colours and/or different trigger temperatures.

The time it takes for the colour change to occur may at least for some applications be of importance. For example it may be desired that the change of temperature occurs in less than 3 seconds, preferably in less than 2 seconds and more preferably in less than 1 second from when the fibres have been exerted to the trigger temperature. A high impact temperature (high above the trigger temperature) on the thermochromic fibres will give a faster colour change than a low impact temperature (close to the trigger temperature).

The thermochromic fibres are preferably colourless, or the same colour as, i.e. do not contrast to, the surrounding material, below a certain temperature, which preferably exceeds normal room, transport and storage temperatures and also lower than the temperatures to which the articles are exerted during manufacturing, except for the triggering step. When a specific temperature threshold is crossed the thermochromic fibres change colour and become visible and in contrast to the surrounding material. This temperature threshold should be slightly below the temperature that the components are exerted to during the triggering process step. "Slightly below" in this context means at least 10° C., preferably between 10 and 30° C., lower than said temperature to which the components are exerted during the triggering step.

A suitable temperature threshold can be in the interval 45 and 150° C., preferably between 50 and 130° C., more preferably between 50 and 120° C. and most preferably between 60 and 120° C. As described above the choice of solvent reaction medium of the thermochromic pigment determines the temperature of the colouring reaction to occur. This is for example described in U.S. Pat. No. 4,826,550 and U.S. Pat. No. 5,197,958.

It is pointed out that the present disclosure is not limited to the embodiments described above and shown in the drawings, but that a plurality of modifications are possible within the scope of the claims.

The invention claimed is:

1. A method for manufacturing an absorbent hygiene article comprising a plurality of components that are joined together during the manufacturing process, comprising the steps of:
   a) incorporating thermochromic fibres to said process in a component web, component or area thereof, said thermochromic fibres being adapted to change colour between a contrasting colour and a less contrasting colour with respect the surrounding parts of the article;
   b) inducing a colour change of said thermochromic fibres during a step of the manufacturing process;
   c) detecting by a detection element the presence of the thermochromic fibres being in their contrasting detectable colour state; and
   d) actuating a measure in response to the presence of said thermochromic fibres being in their contrasting colour state.

2. The method as claimed in claim 1, wherein the colour change of the thermochromic fibres is induced prior to the detection step, wherein the thermochromic fibres will change to their contrasting colour that is detectable by said detection element.

3. The method as claimed in claim 2, wherein the colour change is reversible and returns to the less contrasting colour after detection by said detection element.

4. The method as claimed in claim 2, wherein data is submitted from said detection element to control element for control of a process step and/or a process parameter; said process step and/or process parameter being controlled in response to the data submitted from the detection element.

5. The method as claimed in claim 2, wherein the position and/or configuration of a colour detected area provided by said thermochromic fibres is controlled by a control element compared with a set value and/or detected location of a component of said article, said control element inducing adjustment of one or more process steps and/or process parameters when the position and/or configuration of said colour detected area deviates from said set value and/or said detected location.

6. The method as claimed in claim 2, wherein the position of a colour detected area provided by said thermochromic fibres is used as a synchronizing mark for joining two or more components of the article together in selected areas.

7. The method as claimed in claim 2, wherein the position and/or configuration of a colour detected area provided by said thermochromic fibres is by a control element compared with a set value and/or detected location of a component of said article and that an alarm signal is generated when the position and/or configuration of said colour detected area deviates from said set value and/or said detected location.

8. The method as claimed in claim 1, wherein the thermochromic fibres incorporated in said article have a contrasting colour that is detectable by said detection element and that the colour change of the thermochromic fibres to the less contrasting color is induced after the detection step.

9. The method as claimed in claim 8, wherein the colour change is irreversible and such that the thermochromic fibres become less contrasting to the surrounding areas of the article.

10. The method as claimed in claim 8, wherein data is submitted from said detection element to control element for control of a process step and/or a process parameter; said process step and/or process parameter being controlled in response to the data submitted from the detection element.

11. The method as claimed in claim 8, wherein the position and/or configuration of a colour detected area provided by said thermochromic fibres is controlled by a control element compared with a set value and/or detected location of a component of said article, said control element inducing adjustment of one or more process steps and/or process parameters when the position and/or configuration of said colour detected area deviates from said set value and/or said detected location.

12. The method as claimed in claim 8, wherein the position of a colour detected area provided by said thermochromic fibres is used as a synchronizing mark for joining two or more components of the article together in selected areas.

13. The method as claimed in claim 8, wherein the position and/or configuration of a colour detected area provided by said thermochromic fibres is by a control element compared with a set value and/or detected location of a component of said article and that an alarm signal is generated when the position and/or configuration of said colour detected area deviates from said set value and/or said detected location.

14. The method as claimed in claim 1, wherein data is submitted from said detection element to control element for control of a process step and/or a process parameter; said process step and/or process parameter being controlled in response to the data submitted from the detection element.

15. The method as claimed in claim 1, wherein the position and/or configuration of a colour detected area provided by said thermochromic fibres is controlled by a control element compared with a set value and/or detected location of a component of said article, said control element inducing adjustment of one or more process steps and/or process parameters when the position and/or configuration of said colour detected area deviates from said set value and/or said detected location.

16. The method as claimed in claim 15, wherein said colour detected area is a thermobonding pattern, a weld pattern or a glue pattern, in which the bonding process has induced a colour change in the bonded areas.

17. The method as claimed in claim 15, wherein said process steps and/or process parameters are selected from: temperature, position of a component of the article and/or process equipment, process speed, and stretching of a web material.

18. The method as claimed in claim 1, wherein the position of a colour detected area provided by said thermochromic fibres is used as a synchronizing mark for joining two or more components of the article together in selected areas.

19. The method as claimed in claim 1, wherein the position and/or configuration of a colour detected area provided by said thermochromic fibres is by a control element compared with a set value and/or detected location of a component of said article and that an alarm signal is generated when the position and/or configuration of said colour detected area deviates from said set value and/or said detected location.

20. The method as claimed in claim 1, wherein the thermochromic fibres change colour at a temperature of between 45 and 150° C.

21. The method as claimed in claim 1, wherein the absorbent hygiene article is a diaper, a pant diaper, a sanitary napkin, or an incontinence guard.

* * * * *